United States Patent
Covington et al.

(10) Patent No.: US 6,517,513 B1
(45) Date of Patent: Feb. 11, 2003

(54) INTRADUCTAL BREAST FLUID ASPIRATION DEVICE

(75) Inventors: Chandice Covington, Clinton Township, MI (US); Kevin Morton, Mission Viejo, CA (US)

(73) Assignees: NeoMatrix, LLC, Irvine, CA (US); Wayne State University, Detroit, MI (US)

(*) Notice: Subject to any disclaimer, the term of this patent is extended or adjusted under 35 U.S.C. 154(b) by 0 days.

(21) Appl. No.: 09/488,893

(22) Filed: Jan. 21, 2000

Related U.S. Application Data (60) Provisional application No. 60/116,815, filed on Jan. 21, 1999.

(51) Int. Cl.[7] .................................................. A61M 1/06
(52) U.S. Cl. ............................................................ 604/74
(58) Field of Search .............................. 604/73–76, 131, 604/132, 154, 118, 120, 540

(56) References Cited

U.S. PATENT DOCUMENTS

| | | |
|---|---|---|
| 3,608,540 A | 9/1971 | Sartorius |
| 3,786,801 A | 1/1974 | Sartorius |
| 3,822,703 A | 7/1974 | Davisson |
| 4,249,481 A | 2/1981 | Adams |
| 4,376,053 A | 3/1983 | Bullock et al. |

(List continued on next page.)

FOREIGN PATENT DOCUMENTS

| | | |
|---|---|---|
| WO | WO 98/22160 | 5/1998 |
| WO | WO00/39557 | 7/2000 |
| WO | WO00/42841 | 7/2000 |
| WO | WO00/43038 | 7/2000 |
| WO | WO00/43553 | 7/2000 |
| WO | WO00/70349 | 11/2000 |
| WO | WO00/72766 | 12/2000 |
| WO | WO02/38032 | 5/2002 |

OTHER PUBLICATIONS

ER Sauter, et al.; "Nipple aspirate fluid: a promising non–invasive method to identify cellular markers of breast cancer risk"; British Journal of Cancer (1997) 76(4) pp. 494–501.

Carotenoids of Human Colostrum, Stuart Patton et al., *Lipids*, vol. 25, No. 3, pp. 159–165 (1990).

Cholesterol and Cholesterol Epoxides in Nipple Aspirates of Human Breast Fluid, Nicholas L. Petrakis et al., *Cancer Research*, vol. 41, pp. 2563–2566, Jun. 1981.

Relationship Between Serum Prolactin Levels and Protein Composition of Breast Secretions in Nonlactating Women, Francisco Vizoso et al., *Journal of Clinical Endocrinology and Metabolism*, vol. 79, No. 2, pp. 525–529, 1994.

Evidence for a protective effect of lactation on risk of breast cancer in young women, Results from a case–control study, Anne McTiernan and David B. Thomas, American Journal of Epidemiology, vol. 124, No. 3, 1986.

Independent Protective Effect of Lactation against Breast Cancer: A Case–Control Study in Japan, Keun–Young Yoo, Kazuo Tajima, Tetsuo Kuroishi, Kaoru Hirose, Minoru Yoshida, Shigeto Miura, and Hiroshi Murai, American Journal of Epidemiology, vol., 135, No. 7, 1992.

Epidemiological and Biochemical Support for a Theory on the Cause and Prevention of Breast Cancer, T.G.C. Murrell, Medical Hypothesis, (1991) 36, 389–396.

(List continued on next page.)

*Primary Examiner*—Anhtuan T. Nguyen
(74) *Attorney, Agent, or Firm*—Knobbe Martens Olson & Bear LLP (57) ABSTRACT

Methods and devices are disclosed for reducing the level of carcinogens in the breast, and influencing the transport of blood carotenoids into the intraductal environment. In one embodiment, the device comprises a pump having compression, suction, and heat adapted to optimize noninvasive extraction of intraductal breast fluid during periods of non-lactation, from a parous or nulliparous patient.

59 Claims, 7 Drawing Sheets

Hierarchical Regression For Breast Fluid Carotenoid on Plasma Carotenoid and Cumulative Lifetime Duration of Lactation, Age, Parity, and Length of Time Post-Wean Serving Together as Moderators

| Variable | β | ΔR² | p |
|---|---|---|---|
| Step 1 | | | |
| Plasma Carotenoid | -.38 | .15* | .04 |
| Step 2 | | | |
| Age | .17 | .07 | .77 |
| Cumulative Duration of Lactation | -.08 | | |
| Months Post-Wean | .14 | | |
| Parity | .06 | | |
| Step 3 | | | |
| Plasma Carotenoid x Months Post-Wean | -.62† | .32 | .04 |
| Plasma Carotenoid x Age | -.40 | | |
| Plasma Carotenoid x Cumulative Duration of Lactation | -.20 | | |
| Plasma Carotenoid x Parity | .37 | | |

Note *R²; †ρ = .05, partial = -.45

U.S. PATENT DOCUMENTS

| | | | |
|---|---|---|---|
| 4,393,811 A | 7/1983 | Bodmin | |
| 4,452,779 A | 6/1984 | Cockerill | |
| 4,542,750 A | 9/1985 | Ettare | |
| 4,583,970 A | 4/1986 | Kirschner | 604/74 |
| 4,680,028 A | 7/1987 | Stuart | |
| 4,759,747 A | 7/1988 | Aida et al. | 604/74 |
| 4,761,160 A | 8/1988 | Vermillion | |
| 4,883,464 A | 11/1989 | Morifuki | |
| 4,941,433 A | 7/1990 | Hanauer | |
| 4,964,851 A | 10/1990 | Larsson | |
| 5,007,899 A | 4/1991 | Larsson | |
| 5,049,126 A | 9/1991 | Larsson | |
| 5,071,403 A | 12/1991 | Larsson | 604/74 |
| 5,110,557 A | 5/1992 | Brown et al. | 422/101 |
| 5,476,492 A | 12/1995 | Unrug | |
| 5,482,004 A | 1/1996 | Chowdhury | |
| 5,493,995 A | 2/1996 | Chowdhurry | |
| RE35,316 E | 8/1996 | Negersmith et al. | 210/798 |
| 5,576,329 A | 11/1996 | Hennessey | |
| 5,627,034 A | 5/1997 | Gould et al. | |
| 5,628,964 A | 5/1997 | Tassitano | 422/101 |
| 5,645,537 A | 7/1997 | Powles et al. | |
| 5,664,984 A | 9/1997 | Laughridge | |
| 5,720,722 A | 2/1998 | Lockridge | |
| 5,741,649 A | 4/1998 | Inazawa | |
| 5,776,098 A | 7/1998 | Silver et al. | |
| 5,776,177 A | 7/1998 | MacWhinnie et al. | |
| 5,797,875 A | 8/1998 | Silver | |
| 5,798,266 A | 8/1998 | Quay et al. | |
| 5,810,772 A * | 9/1998 | Niederberger | 604/74 |
| 5,810,796 A | 9/1998 | Kimura et al. | |
| 5,846,739 A | 12/1998 | Gould et al. | |
| 5,855,889 A | 1/1999 | Watson et al. | |
| 5,885,246 A | 3/1999 | Ford | |
| 5,895,640 A | 4/1999 | Khalkhali | |
| 5,902,267 A | 5/1999 | Medo | |
| 5,902,279 A | 5/1999 | Powles et al. | |
| 5,913,686 A | 6/1999 | Van Winkle | |
| 5,914,238 A | 6/1999 | Keesee et al. | |
| 5,922,836 A | 7/1999 | Watson et al. | |
| 5,941,847 A | 8/1999 | Huber et al. | |
| 6,004,186 A | 12/1999 | Penny | |
| 6,004,756 A | 12/1999 | Watson et al. | |
| 6,063,029 A | 5/2000 | Saita et al. | |
| 6,110,140 A | 8/2000 | Silver | |
| 6,168,779 B1 | 1/2001 | Barsky et al. | 424/9.2 |
| 6,221,622 B1 | 4/2001 | Love | 437/7.23 |
| 6,287,521 B1 | 9/2001 | Quay et al. | |
| 6,314,315 B1 | 11/2001 | Hung et al. | 600/547 |
| 6,316,189 B1 | 11/2001 | Haddad et al. | |
| 6,316,215 B1 | 11/2001 | Adair et al. | |
| 6,328,709 B1 | 12/2001 | Hung et al. | 604/74 |
| 6,358,226 B1 | 3/2002 | Ryan | 604/74 |
| 6,379,327 B2 | 4/2002 | Lundy | 604/74 |
| 6,383,163 B1 * | 5/2002 | Kelly et al. | 604/74 |
| 6,383,164 B1 | 5/2002 | Johansen et al. | 604/74 |
| 6,391,026 B1 | 5/2002 | Hung et al. | 606/41 |
| 6,398,765 B1 | 6/2002 | Hung | 604/284 |
| 6,413,228 B1 | 7/2002 | Hung et al. | 600/562 |
| 2001/0001059 A1 | 5/2001 | Love | 435/7.1 |
| 2001/0034038 A1 | 10/2001 | Hung | |
| 2001/0039015 A1 | 11/2001 | Sauter | |
| 2001/0047148 A1 | 11/2001 | Suh | 604/74 |
| 2002/0002343 A1 | 1/2002 | Hung et al. | |
| 2002/0007115 A1 | 1/2002 | Hung et al. | |
| 2002/0010405 A1 | 1/2002 | Hung et al. | |
| 2002/0013539 A1 | 1/2002 | Hung | |
| 2002/0019017 A1 | 2/2002 | Love et al. | 435/7.23 |
| 2002/0037265 A1 | 3/2002 | Hung et al. | 424/70.1 |
| 2002/0045162 A1 | 4/2002 | Hung | 435/5 |
| 2002/0058887 A1 | 5/2002 | Soito et al. | 600/573 |
| 2002/0062103 A1 | 5/2002 | Larsson et al. | 604/74 |
| 2002/0072702 A1 | 6/2002 | Quay | 604/74 |
| 2002/0086341 A1 | 7/2002 | Nguyen | 435/7.23 |

OTHER PUBLICATIONS

McTiernan, A., & Thomas, D. (1986). Evidence of a protective effort of lactation on risk of breast cancer in young women. *American Journal of Epidemiology*, 124, 353–358.

Murrell, T. (1991). Epidemiological and biochemical support for a theory on the cause and prevention of breast cancer. *Medical Hypotehses*, 36, 389–396.

Yoo, K–Y., Tajima, K., Kuroishi, T., Hirosi, K., Yoshida, M., Miura, S., & Murai, H. (1992). Independent protective effect of lactation against breast cancer. A cast–control study in Japan. *American Journal of Epidermiology*, 135, 725–733.

Nipple Aspirate Fluid in Epidemiologic Studies of Breast Disease, Nicholas L. Petrakis, *Epidemiologic Reviews*, vol. 15, No. 1, pp. 188–195 (1993).

Exfoliative Cytology of the Human Mammary Gland and Its Value in the Diagnosis of Cancer and Other Diseases of the Breast, George N. Papanicolaou, M.D., Ph.D., et al., *Cancer*, vol. 11, No. 2, pp. 377–409, Mar.–Apr. 1958.

Breast Cancer Incidence in Women with Abnormal Cytology in Nipple Aspirates of Breast Fluid, Margaret R. Wrensch et al., *American Journal of Epidemiology*, vol. 135,, No. 2, 1992.

Mutagenic Activity in Nipple Aspirates of Human Breast Fluid, Nicholas L. Petrakis et al., *Cancer Research*, vol. 40, 188–189.

"Final Results of Ductal Lavage Study Presented AT 23rd Annual San Antonio Breast Cancer Symposium: Pre–malignant and Malignant Cells Detected in Women at High–risk for Breast Cancer"; http://www.ductallavage.com/Product/Text/San_Antonio_release.html.

"Lancet Study Shows Promising New Breast Cancer Research Application Using Ductal Lavage" http://www-.ductallavage.com/Product/Text/FINALPDHLancetreleased4.26.01htm.

"Study Demonstrates Ductal Lavage Collects Abnormal Breast Cells That Can Help Assess Breast Cancer Risk"; http://www.ductallavage.com/Product/Text/acog.htm; *University Physicians Medical Group*.

IHS® Health Goup Midical Industry Today.htm; Study: Ductal Lavage Shows Promise in Breast Cancer Detection.

U.S. patent application Ser. No. 09/488,905, Covington, filed Jan. 21, 2000.

Adami et al., "Absence of association between reproductive variables and the risk of breast cancer in young women in Sweden and Norway," *British Journal of Cancer*, vol. 62, pp. 122–126 1990.

America Cancer Society *Cancer facts and figures*, 1996.

American Cancer Society *Breast cancer facts and figures*, 1996.

Anderson et al., *Cancer*, vol. 65, 1901–1908, 1989.

Basu et al., "Serum vitamins A and E, beta–carotene, and selenium in patients with breast cancer," *Journal of the American College of Nutrition*, vol. 8, pp. 524–529 1989.

Bendich et al., "Antioxidant nutrients and immune function," *Advances in Experimental Medicine and Biology*, vol. 262, New York: Plenum Press 1990.

Brisson et al., "Diet, mammographic features of breast tissue, and breast cancer risk," *American Journal of Epidemiology*, vol. 130, pp. 14–24 1989.

Britton et al., *Carotenoids Vol. 1a: Isolation and analysis.* Basel: Birkhausen Verlag 1995.

Burton et al., "Antioxidant action of carotenoids," *Journal of Nutrition*, vol. 119, pp. 109–115 1989.

Burton et al., "Beta–carotene: An unusual type of lipid antioxidant," *Science*, vol. 224, pp. 569 1984.

Byers et al., "Dietary carotenes, vitamin C, and vitamin E as protective antioxidants in human cancers," *Annual Review of Nutrition*, vol. 12, pp. 139–159 1992.

Byers et al. "Lactation and breast cancer," *American Journal of Epidemiology*, vol. 121, pp. 139–159 1985.

Dawood et al., *American Journal of Obstetrics and Gynecology*, 138, 20–245, 1980.

DeLuca, "Vitamin A" in: *The fat–soluble vitamins*, H. Deluca (Ed.), p. 1–67, New York; Plenum Press. 1978.

Di Mascio et al., "Antioxidant defense systems: The role of carotenoids, tocopherols, and thiols," *American Journal of Clinical Nutrition*, vol. 53, pp. 194–200 1991.

Ewertz et al., "Dietary factors and breast–cancer risk in Denmark," *International Journal of Cancer*, vol. 46, pp. 779–784 1990.

Gaitan et al., *Endocrinology*, Sep, S1(3), 515–520, 1967.

Greiner *Pharmaceutical Tech.*, May 1993, pp. 28–44 1993.

Haagensen et al., *Breast carcinoma: Risk and detection*, Philadelphia: W.B. Saunders Company 1981.

Hill et al., "Retinoids and Cancer Prevention," *Annu. Rev. Nutr.* vol. 12, pp. 161–181 1992.

Hislop et al., "Diet and histologic types of benign breast disease defined by subsequent risk of breast cancer," *American Journal of Epidemiology*, vol. 131, pp. 263–270 1990.

Holmes et al., "Dietary guidelines " In: *Reducing breast cancer in women*, B. Stoll (Ed.), pp. 135–144 1995.

Inaji et al., *Cancer* vol. 60, 3008–3013 1987.

Ing et al., "Unilateral breast feeding and breast cancer," *The Lancet*, vol. 7, pp. 124–127 1977.

Katsouyanni et al., "Risk of breast cancer among Greek women in relation to nutrition intake," *Cancer*, vol. 61, pp. 181–185 1988.

Kinsel et al., *Cancer Res.* 49: 1052–1056, 1989.

Knecht et al., "Serum vitamin A and subsequent risk of cancer: Cancer incidence follow–up of the finish mobile clinic health examination survey," *American Journal of Epidemiology*, vol. 132, pp. 857–870 1990.

Krinsky et al., "Interaction of oxygen and oxy–radicals with carotenoids," *Journal of the National Cancer Institute*, vol. 69, pp. 205 1982.

Krinsky, "Actions of Cartoenoids in Biological Systems," *Annu. Rev. Nutr*, vol. 13, pp. 561–587 1993.

Kvale et al., "Lactation and cancer risk: Is there a relationship specific to breast cancer," *Journal of Epidemiology and Community Health*, vol. 42, pp. 30–37 1987.

Layde et al., "The independent association of parity, age at first full–term pregnancy, and duration of breastfeeding with the risk of breast cancer," *Journal of Clinical Epidermiology*, vol. 42, pp. 963–973 1988.

Levin et al., "Lactation and menstrual function as related to cancer of the breast," *American Journal of Public Health*, vol. 54, pp. 580 1964.

Love, "Introduction" In: *Reducing breast cancer risk in women*, B. Stoll (Ed.), 1995.

Lubin et al., "Risk factors for breast cancer in women in Northern Alberta Canada as related to age at diagnosis," *Journal of the National Cancer Institute*, vol. 68, pp. 211–217 1992.

MacMahon et al., "Lactation and cancer of the breast: a summary of an international study," *Bulletin of the World Health Organization*, vol. 42, pp. 85 1970.

Marubini et al., "The relationship of dietary intake and serum levels of retinol and beta–carotene with breast cancer," *Cancer*, vol. 61, pp. 173–180 1988.

Matthews–Roth, *Curr. Top. Nutr. Dis.* (*New Prot. Roles Select Nurt.*) vol. 22, pp. 17–38 1989.

Matthews–Roth, *Pure Appl. Chem.* vol. 57, pp. 717–722 1985.

Michnovicz et al., *How to reduce your risk of breast cancer.*, New York: Warner Books 1994.

Mori et al., *Jpn. J. Clin. Oncol.* 19: 373–379 1989.

Negri et al., "Intake of selected micronutrients and the risk of breast cancer," *International Journal of Cancer* vol. 65, pp. 140–144 1995.

Newcomb et al., "Lactatation and a reduced risk of pre-menopausal breast cancer," *New England Journal of Medicine*, vol. 330, pp. 81–87 1994.

Paganini–Hill et al., "Vitamin A, beta–carotene, and the risk of cancer: A prospective study," *Journal of the National Cancer Institute* vol. 79, pp. 443–448 1987.

Parl et al., *Hum. Pathol.* 19: 960–966, 1988.

Pertschuk et al., *Cancer*, vol. 66, 1663–1670 1990.

Petrakis et al., "Association of breast fluid coloration with age, ethnicity, and cigarette smoking," *Breast Cancer Research and Treatment*, vol. 11, pp. 255–262 1988.

Petrakis et al., "Association of race, age, menopausal status, and cerumen type with breast fluid secretion in non–lactating women as determined by nipple aspiration," *Journal of the National Cancer Institute*, vol. 54, pp. 829–833 1975.

Petrakis et al., "Cerumen phenotype and proliferative epithelium in breast fluids of U.S.–Born immigrant Asian women: A possible genetic–environmental interaction," *Breast Cancer Research and Treatment* vol. 16, pp. 279–285 1990.

Petrakis et al., "Coloration of breast fluid related to concentration of cholesterol, cholesterol epoxides, estrogen, and lipid peroxides," *American Journal of Clinical Pathology*, vol. 89, pp. 117–120 1988.

Petrakis et al., "Nipple aspirate fluids in adult non–lactating women–lactose content, cationic Na+, K+, Na+/K+ ratio, and coloration," *Breast Cancer Research and Treatment*, vol. 13, pp. 71–78 1989.

Petrakis, "Nipple Aspirate Fluid in Epidemiologic Studies of Breast Disease", *Epidermiologic Reviews*, vol. 15, No. 1, pp. 188–195 (1993).

Petrakis, "Physiologic, biochemical, and cytologic aspects of nipple aspirate fluid," *Breast Cancer Research and Treatments*, vol. 8, pp. 7–9 1986.

Petro et al., *Nature*, 1981, 290, 201–208.

Pitt "Vitamin A" In: *Fat soluble vitamins: Their biochemistry and applications*, A. Diplock (Ed.), pp. 1–75, London: Heinemann 1985.

Porter–Jordan et al., *Hematol. Oncol. Clin. North Amer.* 8: 73–100 1994.

Potishman et al., "Breast cancer and dietary and plasma concentrations of carotenoids and vitamin A," *American Journal of Clinical Nutrition*, vol. 52, pp. 909–915 1990.

Rohan et al., A population based case–control study of diet and breast cancer in Australia *American Journal of Epidemiology*, vol. 128, pp. 478–489 1988.

Sarhadi et al., *Br J Plast Surg*, (8): 668–670, 1997.

Sartorius "Breast fluid cells help in early cancer detection," *Journal of the American Medical Association*, vol. 224, pp. 823–827 1973.

Sartorius et al., "Cytologic evaluation of breast fluid in the detection of breast disease," *Journal of the National Cancer Institute*, vol. 59, pp. 1073–1078 1977.

Sauter, et al.; "Nipple aspirate fluid: a promising non–invasive method to identify cellular markers of breast cancer risk"; British Journal of Cancer (1997) 76(4) pp. 494–501.

Seoud et al., *J. Reprod Med.*, 38(6), 438–442, 1993.

Siskind et al., "Breast cancer and breastfeeding: Results form an Australian case–control study," *American Journal of Epidemiology*, vol. 130, pp. 229–236 1988.

Taylor–Papadimitriou et al., "Cell lineage and interactions in neoplastic expression in the human breast," In: *Understanding Breast Cancer*, M. Rich, J. Hager, & P. Furmanski (Eds.), pp. 215–246, New York: Marcek Dekker, Inc. 1983.

Van't Veer et al., "Dietary fiber, beta–carotene, and breast cancer: Results from a case–control study," *International Journal of Cancer*, vol. 45, pp. 825–828 1990.

Visozo et al., "Factors affecting protein composition of breast secretions from nonlactating women," *Breast Cancer Research*, vol. 23, pp. 251–258 1992.

Wald et al., "Plasma retinol, beta–carotene, and vitamin E. levels in relation to further risk of breast cancer," *British Journal of Cancer*, vol. 49, pp. 321–324 1984.

Weisberger "Nutritional approach to cancer prevention with emphasis on vitamins, antioxidants, and carotenoids," *American Journal of Clinical Nutrition*, vol. 53, pp. 226–237 1991.

Wrensch et al., "Factors associated with obligating nipple aspirate fluid: Analysis of 1428 women and literature reviews," *Breast Cancer Research and Treatment*, vol. 15, pp. 39–51 1990.

Yuan et al., "Risk factors for breast cancer in Chinese women in Shanghai," *Cancer Research*, vol. 48, pp. 1949–1953 1988.

\* cited by examiner

Hierarchical Regression For Breast Fluid Carotenoid on Plasma Carotenoid and Age

| Variable | β | ΔR² | p |
|---|---|---|---|
| Step 1<br>    Plasma Carotenoid | -.37 | .13* | .02 |
| Step 2<br>    Age | .21 | .04 | .17 |
| Step 3<br>    Plasma Carotenoid<br>       x Age | -.33 | .10 | .03† |

Note *R²; †partial = .35

*FIG. 1*

Hierarchical Regression For Breast Fluid Carotenoid on Plasma Carotenoid and Parity

| Variable | β | ΔR² | p |
|---|---|---|---|
| Step 1<br>    Plasma Carotenoid | -.37 | .13* | .02 |
| Step 2<br>    Parity | .05 | .003 | .72 |
| Step 3<br>    Plasma Carotenoid<br>       x Parity | -.11 | .01 | .47 |

Note *R²

*FIG. 2*

Hierarchical Regression For Breast Fluid Carotenoid on Plasma Carotenoid and Length of Time Post-Wean

| Variable | β | ΔR² | p |
|---|---|---|---|
| Step 1 Plasma Carotenoid | -.39 | .16* | .03 |
| Step 2 Months Post-Wean | .18 | .03 | .36 |
| Step 3 Plasma Carotenoid x Months Post-Wean | -.48 | .21 | .007† |

Note *R²; †partial=-.51

FIG.3

Hierarchical Regression For Breast Fluid Carotenoid on Plasma Carotenoid and Lactation, Age, Parity, and Length of Time Post-Wean Serving Together as Moderators

| Variable | β | ΔR² | p |
|---|---|---|---|
| Step 1 Plasma Carotenoid | -.38 | .15* | .04 |
| Step 2 Age | .18 | .07 | .78 |
| Lactation | -.03 | | |
| Months Post-Wean | .15 | | |
| Parity | .002 | | |
| Step 3 Plasma Carotenoid x Months Post-Wean | -.59† | .31 | .05 |
| Plasma Carotenoid x Age | -.40 | | |
| Plasma Carotenoid x Lactation | -.16 | | |
| Plasma Carotenoid x Parity | .31 | | |

Note *R²; †p = .04, partial = -.47

FIG.6

Hierarchical Regression For Breast Fluid Carotenoid on Plasma Carotenoid and Lactation

| Variable | β | ΔR² | ρ |
|---|---|---|---|
| Step 1<br>Plasma Carotenoid | -.37 | .14* | .008 |
| Step 2<br>Lactation | -.16 | .03 | .14 |
| Step 3<br>Plasma Carotenoid<br>x Lactation | .20 | .04 | .09† |

Note *R²; †partial = .21

FIG.4

Hierarchical Regression For Breast Fluid Carotenoid on Plasma Carotenoid and Cumulative Lifetime Duration of Lactation

| Variable | β | ΔR² | ρ |
|---|---|---|---|
| Step 1<br>Plasma Carotenoid | -.36 | .13* | .02 |
| Step 2<br>Cumulative Duration<br>of Lactation | .07 | .004 | .34 |
| Step 3<br>Plasma Carotenoid<br>x<br>Cumulative Duration<br>of Lactation | .07 | .004 | .34 |

Note *R²

FIG.5

Hierarchical Regression For Breast Fluid Carotenoid on Plasma Carotenoid and Cumulative Lifetime Duration of Lactation, Age, Parity, and Length of Time Post-Wean Serving Together as Moderators

| Variable | β | $\Delta R^2$ | $p$ |
|---|---|---|---|
| Step 1 | | | |
| Plasma Carotenoid | -.38 | .15* | .04 |
| Step 2 | | | |
| Age | .17 | .07 | .77 |
| Cumulative Duration of Lactation | -.08 | | |
| Months Post-Wean | .14 | | |
| Parity | .06 | | |
| Step 3 | | | |
| Plasma Carotenoid x Months Post-Wean | -.62† | .32 | .04 |
| Plasma Carotenoid x Age | -.40 | | |
| Plasma Carotenoid x Cumulative Duration of Lactation | -.20 | | |
| Plasma Carotenoid x Parity | .37 | | |

Note *$R^2$; †$p = .05$, partial $= -.45$

INTRADUCTAL BREAST FLUID ASPIRATION DEVICE

This application claims priority of U.S. Provisional Patent Application Ser. No. 60/116,815, filed Jan. 21, 1999, the disclosure of which is incorporated in its entirety herein by reference.

The present invention was made with U.S. Government support under NIH grant NR03142. The U.S. Government has certain rights in the invention.

BACKGROUND OF THE INVENTION

The present invention relates to the reduction of breast cancer risk, and, in particular, to methods and devices for influencing the transport of carotenoids and possibly other substances from the blood into the breast microenvironment.

Breast cancer is one of the leading causes of disease and death in women, with greater than 90% of breast cancer originating in the epithelial cells of ducts (American Cancer Society, 1996a). Early detection and treatment of breast cancer has focused on improving prognosis and increasing the survival rates, still such rates have only plateaued (American Cancer Society, 1996d). As a result, women's health experts have instigated a renewed focus and call for innovation in breast cancer prevention efforts (Love, 1995).

The protective effect of lactation and dietary carotenoids in breast cancer development has been supported (American Cancer Society, 1996a; Holmes, Hunter, & Willett, 1995; Stoll, 996; Weisburger, 1991). Little is known, however, about the influence the naturally-occurring physiologic process of lactation has on the microenvironment of the breast in relation to breast cancer prevention. Less is known about the presence of carotenoids in the microenvironment of the breast. No information is available on how lactation might influence transport of carotenoids into the microenvironment of the breast. Yet, lactation and diet as protective or chemopreventive processes represent health choices for women to prevent breast cancer.

The presence of fluid in the breast has been confirmed by history in the breast has been confirmed by histological study of the breast ductal system (Petrakis et al., 1975), and breast fluid has been obtained through manual aspiration from parous and nulliparous women (Petrakis et al., 1975; Sartorius, 1973, Sartorius, Smith, Morris, Benedict, & Friesen, 1977). Sartorious (1973) first reported the use of a suction device to aspirate breast fluid in a report on devising methods to detect breast cancer by studying cells from the breast fluid.

Petrakis et al. (1975, 1986, 1988a, 1988b, 1989, 1990), Sartorius et al. (1977), Visozo et al. (1992), and Wrensch et al. (1990) have conducted several studies ranging from clinical availability of breast secretions, descriptions of breast fluid regarding content, to epidemiologic investigations into cytologic changes and breast disease. These studies have supported that the epithelial lining of the breast ducts exist in a fluid environment that reflects the internal and external environment of the human. Murrell (1991) has hypothesized that under normal physiologic conditions, damage to breast epithelium by carcinogens as products of oxygen free radicals, in the absence of stimulus to clear fluid containing carcinogens, may expose the breast to increased risk of cancer development.

During the physiologic process of lactation, the fluid microenvironment of the breast is in a repetitious process of fluid synthesis and drainage. Changes in the breast epithelium lining the ducts during differentiation and growth in preparation for milk production is thought to alter the susceptibility of the cell to neoplastic changes (McTiernan & Thomas, 1986; Taylor-Papadimitriou, Lane, & Change, 1983). Furthermore, lactation acting as a mechanical cleansing process, flushes potential carcinogens in the ducts, which may represent another way in which lactation decreases risk of breast cancer (McTiernan & Thomas, 1986; Murrell, 1991; Yoo, et al., 1992). Malhotra (1977) points out that an alkaline milieu at the breast epithelial cell level results in increased mitotic activity and cell proliferation, which is carcinogenic. Stasis in the fluid environment of the breast, which can specifically occur during lactation failure, maintains the alkalinity of the cell environment. Nipple stimulation, which would likely increase oxytocin levels and lead to drainage of the breast, may be instrumental in preventing breast disease (Murrell, 1991).

While past studies on the protective effect of lactation on breast cancer risk report mixed results from nonconsequential (Haagensen et al., 1981; Kvale and Heuch, 1987; MacMahon et al., 1970) to moderate (Adami et al., 1990; Ing, Ho, and Petrakis, 1977; Levin, Sheehe, Graham, and Glidwell, 1964; Malhotra, 1977; McTierman and Thomas, 1986; Siskind et al., 1988), results from several contemporary studies support an association between lactation and decreased breast cancer risk, suggesting an independent, protective effect (Byers et al., 1985; Layde et al., 1988; Lubin et al., 1992; Newcomb et al., 1994; Yoo et al., 1992; Yuan et al., 1988). Most studies did not operationalize lactation other than in a dichotomous fashion (yes/no). Cumulative length of lactation can vary greatly among women.

Carotenoids are a group of related chemicals and natural lipid-soluble pigments found mainly in plants, certain vegetables, and in animal tissue (Britton, Liaaen-Jansen, & Pfander, 1995; DeLuca, 1978; Michnovicz & Klein, 1994) and serve as precursors of vitamin A. Of the carotenoids with provitamin A activity, beta-carotene "is the most common and most effective" (Pitt, 1985, p. 8), thus beta-carotene has become the focus of interest as a significant biologically-active nutritional and anticarcinogenic substances (Burton, 1989; Byers & Perry, 1992; Dimascio, Murphy, & Sies, 1991). The main function of antioxidant nutrition, which includes lipid-soluble molecules such as carotenoids and enzymes derived from minerals, is to prevent oxidative damage to cells and their physiological function. Beta-carotene is the major carotenoid precursor of vitamin A and is the most effective, naturally occurring single oxygen quencher (Bendich, Phillips, and Tengerdy, 1990; Burton, 1989; Burton & Ingold, 1984; Krinsky & Deneke, 1982).

Of 15 studies investigating the relationship between nutrient intake and risk of cancer, including breast cancer, six studies (Brisson et al. 1989; Katsouyanni et al. 1988; Knecht et al., 1990; Negri et al., 1995; Rohan, McMichael, & Bahurste, 1988; & Wald et al, 1984), reported a decreased risk of breast cancer with dietary intake of beta-carotene. In seven studies, (Basu et al., 1989; Ewertz & Gill, 1990; Hislop, 1990; Marubini et al., 1988; Paganini-Hill et al., 1978; Potishman et al., 1990; Van'tNeer et al., 1990), results did not support the protective effect of beta-carotene. However, methods used to index or provide beta carotene intake are fraught with error, such as controlling for cooking methods or lipid intake, which is necessary for utilization of beta carotene.

Patton, et al. (1990) identified and measured concentrations of carotenoids in human colostrum in women immediately postpartum, specifically alpha- and beta-carotene, lycopene, and beta-cryptoxanthin. The concentrations of these carotenoids were widely varied and decreased over the first week postpartum, suggesting a flushing and diluting effect of progressive lactation on substances that are normally stored in the resting breast. Covington, et al. (1998) reported the presence of carotenoids in post-weaned breast fluids. Additionally, length of time post-wean negatively influenced the carotenoid level in nipple aspirates, while cumulative duration of lactation was not significantly related to carotenoid levels.

Notwithstanding the extensive research which has been conducted in this field, there remains a need for an understanding of the role of intraductal fluid and in connection with the risk of breast cancer, as well as methods and devices for using that understanding to create an efficacious risk reduction regimen.

SUMMARY OF THE INVENTION

There is provided in accordance with one aspect of the present invention, a method of elevating intraductal carotenoid levels in a non-lactating breast in a patient. The method comprises the steps of removing intraductal breast fluid from the non-lactating breast over a predetermined regimen. Although any removal of intraductal breast fluid in accordance with the present invention may have some preventative effects, removal is preferably accomplished in a series such as at least once per month, preferably twice per month or once per week over a period of at least two to six months.

In one embodiment of the invention, the removing intraductal breast fluid comprises manual aspiration. Preferably, the removing step comprises the steps of applying suction and compression. In one embodiment, the method further comprises the step of applying heat. Preferably, the compression comprises peristaltic compression.

The method may additionally comprise the step of increasing the oxytocin level in the breast prior to the removing step. The oxytocin level may be increased by direct administration of oxytocin to the patient, and/or by nipple stimulation.

In accordance with a further aspect of the present invention, there is provided a method of removing intraductal breast fluid from a patient. The method comprises the steps of contacting the breast with a mechanical intraductal fluid aspiration device, and activating the device to apply peristaltic compression and suction to the breast during a period of non-lactation to removal intraductal breast fluid. Preferably, the method additionally comprises the step of applying heat from the device to the breast.

In accordance with another aspect of the present invention, there is provided a method of reducing the risk of cancer formation in the breast duct. The method comprises the steps of periodically removing intraductal breast fluid from the breast using a mechanical intraductal breast fluid removal device. This may maintain an elevated average carotenoid level in the breast fluid compared to the carotenoid level in the absence of intraductal breast fluid removal. Preferably, the elevated average carotenoid level is maintained for a period of at least about 30 and preferably at least about 90 days.

In accordance with a further aspect of the present invention, there is provided an intraductal breast fluid aspiration device. The device comprises a tissue contacting surface, defining a first concavity for receiving a breast and a second concavity for receiving a nipple. A driver is provided, for imparting compressive force on at least the portion of the tissue contacting surface defining the first concavity. A vacuum conduit is placed in communication with the second concavity, and a sample collector is in communication with the second concavity.

Preferably, the driver imparts peristaltic compressive force on the tissue contacting surface. In one embodiment, the driver comprises a motor. In another embodiment, the driver comprises at least one expandable chamber such as the area inside an inflatable and collapsible flexible bladder or tube. Preferably, a plurality of inflatable tubes are aligned such that sequential filling and emptying of the tubes provides a peristaltic compressive force on the tissue contacting surface. The intraductal breast fluid aspiration device may additionally be provided with a heat source, such as an ultrasonic transducer.

The sample collector in one embodiment comprises a hollow container, which may be removably attached to the aspiration device. Alternatively, the sample collector comprises an absorbent media or membrane. In one embodiment, the sample collector additionally comprises a binding system for binding at least one analyte of interest in the breast fluid. The binding system may be chemical or biochemical, such as a monoclonal or polyclonal antibody.

In accordance with a further aspect of the present invention, there is provided a portable, self-contained, intraductal fluid aspiration device. The device comprises a housing, and a breast interface carried by the housing. A vacuum source is provided in communication with the interface, and a compression driver is coupled to the interface. At least one control is provided, for controlling operation of the aspiration device. Preferably, the interface is removably connected to the housing. A fluid reservoir is preferably provided in communication with the interface, and the fluid reservoir may be permanent or removably attached to the housing.

In accordance with a further aspect of the present invention, there is provided an intraductal fluid aspiration device which is adapted for use in the physician office or other clinical setting. The device comprises a control unit, and a power head. A flexible control line connects the power head to the control unit. A disposable user interface is removably attached to the power head, and a vacuum source in the control unit is in communication with the user interface through the control line. A compression cycle generator is provided in force transmitting contact with the user interface. Preferably, the device further comprises an ultrasound transducer in the power head. A central processing unit is preferably provided in the control unit for controlling the delivery of heat, compression and suction through the user interface.

Further features and advantages of the present invention will become apparent from the detailed description of preferred embodiments which follows, when considered together with the attached drawings and claims.

DETAILED DESCRIPTION OF PREFERRED EMBODIMENTS

In the United States, the average women has a 12.5% lifetime risk of developing invasive breast cancer. The breast is the leading site of cancer among American women, with over 180,000 new diagnoses annually and approximately 44,000 annual deaths. Incidence trends in the United States between 1983 and 1993 show in situ breast cancer rates increased from 2.3 to 6.2 per 100,000 among women under 50, and from 14.3 to 54.6 per 100,000 in women 50 and older. Additionally, ductal carcinoma in situ (DCIS) has increased markedly from 2.4 per 100,000 in 1973 to 15.8 per 100,000 in 1992.

Virtually all breast cancers originate in the epithelial cells that line the walls of the fluid ducts that are present in a women's breast. The study conducted by the present inventors illustrates routinely high levels of carcinogens, including pesticides and carbon oxides, in the ductal fluid. Damage to the breast duct epithelial cells caused by these carcinogens is recognized to increase the risk of cancer development.

Despite the foregoing, there are currently no approved preventative measures for reducing the incidence of breast cancer, beyond lifestyle changes (such as reducing smoking and regulating diet) that may reduce overall risk. Based upon research conducted by the present inventors, the inventors believes that the routine use of a device that mechanically cleanses the breast ducts, by removing ductal fluid in a manner that biomimics the lactating breast, may become the first preventative measure for reducing the risk of breast cancer.

Intraductal fluid aspiration in accordance with the present invention is preferably made a part of a systematic regimen, such as a monthly routine to be accomplished along with manual examination of the breast for lumps or abnormalities. Specific optimal frequencies and protocols can be determined through routine experimentation by those of skill in the art in view of the disclosure herein.

The present inventors' research has shown the ability to remove carcinogenic intraductal fluid with a biomechanical device, by extracting the intraductal fluid non-invasively through the nipple. The results illustrate that once the intraductal fluid has been removed, replacement fluid is essentially free of carcinogens, and may have an increase in carotinoids, which are believed to have cancer fighting antioxidant properties. Thus, the methods and devices of the present invention enable the decrease of carcinogens in the breast ductal fluids, and a possible corresponding increase in carotinoids, which are expected to have a protective effect from cancer on the breast duct epithelial cells. However, the present invention is not limited to the possible increase in carotinoids as an anti-cancer mechanism. Instead, without limitation as to mechanism, the invention relates more broadly to the periodic or systematic removal of ductal fluid.

In addition to the preventative aspect of the present invention, the present inventors also contemplate a diagnostic use for aspirated intraductal fluid. Noninvasively obtained intraductal fluid may be analyzed in any of a variety of ways, including cytological examination (similar to the Pap smear) or other biochemical or chemical analyses.

The investigation reported below was a descriptive and correctional study designed to evaluate the influence of recent lactation and cumulative lifetime duration of lactation on the relation between plasma and breast fluid carotenoid levels. The influence of age, parity, and length of time post-wean on the relation between plasma and breast fluid carotenoid levels was also investigated. A power analysis for multiple regression (Cohen, 1988) for power of 0.8 and a moderate population effect was completed, and given the preliminary and exploratory nature of this study, an alpha was set at 0.10 (Lutz, 1983). One- and two-tailed tests of significance were used depending on the directional nature of the hypotheses.

Recent lactation is the number of calendar months a women breastfed her last child, reported as a continuous variable from zero months (no lactation) to a specified number of calendar months breastfeeding (lactation). Cumulative lifetime duration of lactation is the sum total number of calendar months a woman breastfed all children. Length of time post-wean is the number of calendar months a woman stopped breastfeeding her last child to the time of participation in this study. Carotenoids are chemopreventive nutrients measurable in plasma and breast fluid using spectrophotometric techniques. Plasma carotenoid level is the measure of total carotenoid (mcg/ml) in the plasma, determined by spectrophotometry. Breast fluid carotenoid level is the measure of total carotenoid (mcg/ml) in breast fluid, determined by spectrophotometry. Secretor/Non-Secretor define women who were able to unable to aspirate breast fluid.

Women who were between 18–45 years of and non-pregnant were recruited for participation. Criteria for inclusion for the breastfeeding group included delivery of a full term infant 24 months prior and that child for at least six months, and being totally weaned for at least three months. After cessation of lactation, mammary involution occurs over a three-month period, resulting in a return to a non-secretory alveolar lining (Mepham, 1987). Women participating in this study were minimally three-months post-wean to control for the physiologic changes that occur during lactation and subsequent to cessation of lactation. Criteria for inclusion for the non-breastfeeding group included delivery of a full-term infant 24 months and selection of formula feeding the infant. Exclusion criteria or withdrawal from the study included pregnancy. Recruitment of subjects occurred in three Midwest metropolitan cities through subject referral, study recruitment fliers at women's health clinics, WIC offices, day-care centers, and public health clinics, and advertisements in the newspaper. Over 100 women were recruited to participate in the parent study, however, only 85 women met the inclusion criteria for this study. Of these, 43 (51%) women were able to express breast fluid and had plasma carotenoid available for analysis.

The total sample for the corollary study consisted of 83 women, with 48% from city 1, 33% from city 2, and 19% from city 3. The majority of women were White, but two women (2%) were Black and two (2%) were Hispanic. The mean age of the women was 31.6 years (D=5.2, range 20–44 years), with education level of 63% with women college or a degree, and 14$ completing a graduate degree. The majority of women (96%) reported total household income of over $30,000.

The subset sample of women consisted of 43 women who were able to aspirate breast fluid and had plasma available for analysis. The majority of women were white, but one (2%) was Black. The mean age was 31.9 years (SD=5.3, range 20–40 years), with education level of 81.4% with some college or a degree, and 9.3% completing a graduate degree. The majority of women reported total household income over $30,000.

The subject's mean number of months postpartum was 23.5 months (D=5.1, range 15–36 months), and 23.7 months (D=5.4, range 15–36) for the subset. Gravidity of three (M=2.4, SD=1.3, range 1–6 pregnancies) was reported by 80% of the women in both sample groups. Parity of three (M=2.0, SD=1.0, range 1–6 live births) was reported by 80% of the women, whereas parity of two was reported by a majority of women (35%) in the subset. Within the sample, 37 women (43%) reported zero months breastfeeding, while 45 women (53%) breastfed their last child a mean for six months (SD=6.8, range 0–30 months). In the subset, 14 women (32.6%) reported zero months breastfeeding, while 29 women (67.5%) breastfed their last child a mean of eight months (SD=6.2, range 3–30 months). For breastfeeding women, the mean number of months breastfeeding their last child was 11.0 months (LD=5.4, range 3–30 months), and 12 months in the subset (SD=5.9, range 3–30 months). Women were 3–30 months post-wean (M=12.4, 11.4 subset, SD=5.8 months, 6.2 subset). The mean number of months for cumulative lifetime duration of lactation was 20 (SD=12.0, range 1–63 months), and 15.4 months (SD=14.4, range= 5–63 months) for the subset.

Human subjects approval was obtained and the study was explained to potential participants. An investigator-developed *Health and Lactation History Questionnaire* (HLHQ) was a self-report tool to assess demographics and collect information regarding health and reproductive history. Demographic factors collected by the HLHQ included age, race, education, occupation, and income. Health and reproductive factors, such as pregnancy and lactation history were also collected in the questionnaire. No reliability and content validity information for this instrument has been reported. A nipple aspiration device was designed to assist in the aspiration of breast fluid, based on the original Sartorius (1977) method. A kit containing microtubes and the aspiration device necessary for collection of breast fluid was developed. A breast fluid sample collection protocol using a subject-controlled, nipple aspiration method to obtain breast fluids over a period of 17 days was used. Fluid was stored in amber opaque microtainers to shield against light which degrades carotenoids. Research nurses were trained to teach and assist women to aspirate with demonstration and video training methods. Blood sampling equipment, including alcohol, butterfly needles, and collection tubes containing EDTA and sodium heparin were used to collect blood for carotenoid assay. Plasma was stored in amber opaque microtainers.

Plasma and breast fluid samples were collected in amber microtubes and stored at −70° C. due to the instability of carotenoids in light and higher temperatures over time. Blood was centrifuged immediately after collection and the plasma withdrawn and stored in amber capillary tubes at −70° C. A university-based lab provided the carotenoid analysis of plasma and breast fluids using spectrophotometric technique. A procedure described by Patton, et al. (1990) for the determination of carotenoids in human colostrum samples was used to measure the amount of total carotenoids in plasma and breast fluid samples.

Participants were asked to complete the questionnaire (HLHQ) and to attempt to collect breast fluid every other day for seventeen days. If unable to collect fluid using the aspirator within a 30-minute attempt, subjects were instructed to stop and try again in two days. The first eight collections of breast fluid were pooled into an amber microtube and maintained in the home freezer between collections. An initial blood sample was collected into a tube containing EDTA.

Upon completion of breast fluid collection, the subjects contacted the research assistant for sample collection. At the final visit, the research assistant collected the questionnaire and breast fluid samples. Women received a small incentive for their participation in the study.

Differences between women reporting no lactation, recorded as zero months (0), and women reporting lactation, recorded as x number of months of breastfeeding, on demographic and reproductive characteristics were discerned by t-test analysis. No significant differences between women on age, income, parity, number of months postpartum, and plasma carotenoid levels were evident in the original and subset samples. However, women reporting lactation were significantly higher educated than women reporting no lactation. A significant difference in number of months of recent lactation and cumulative lifetime duration of lactation was reported between the original and subset samples. However, women in the subset were more likely to be breastfeeders, as these women were more successful in obtaining breast fluid.

A total of 83 plasma samples were sent for analysis. A few plasma samples (n=2) were insufficient or lost in transit, resulting in a total of 81 samples. Of these, the mean plasma carotenoid level was 1.83 mcg/ml (SD=0.89, range 0.037–4.50 mcg/ml). The mean plasma carotenoid level reported in this study is consistent with levels reported in epidemiologic studies measuring plasma carotenoid (Potischman, 1990).

Breast fluid was obtained from 68 women (80%), while 14 women (16.5%) were unable to obtain any breast fluid for collection. However, of the 68 women who obtained some volume of breast fluid, only 45 women (54% of the total sample) were able to aspirate a sufficient amount of breast fluid for total carotenoid analysis. Sartorius (1977) reported collection of breast fluid from women is successful in 50% of collection attempts. The total number of women with both plasma and breast fluid carotenoid levels available for analysis numbered 43 (51%). Reproductive and secretor/non-secretor analysis results suggested that the longer a woman breastfed her last child, the more likely she was able to aspirate breast fluid ($p=0.2$). Furthermore, the longer a woman breastfed her last child, the more likely the amount of breast fluid obtained was a sufficient amount for carotenoid analysis ($p=0.001$). The overall mean breast fluid carotenoid level was 1.73 mcg/ml (SD=1.7, range undetectable—10.20 mcg/ml). This finding was consistent with the mean breasts fluid carotenoid level (1.94 mcg/ml) reported by Covington, et al. (1998) for women post weaned.

Figure 1:
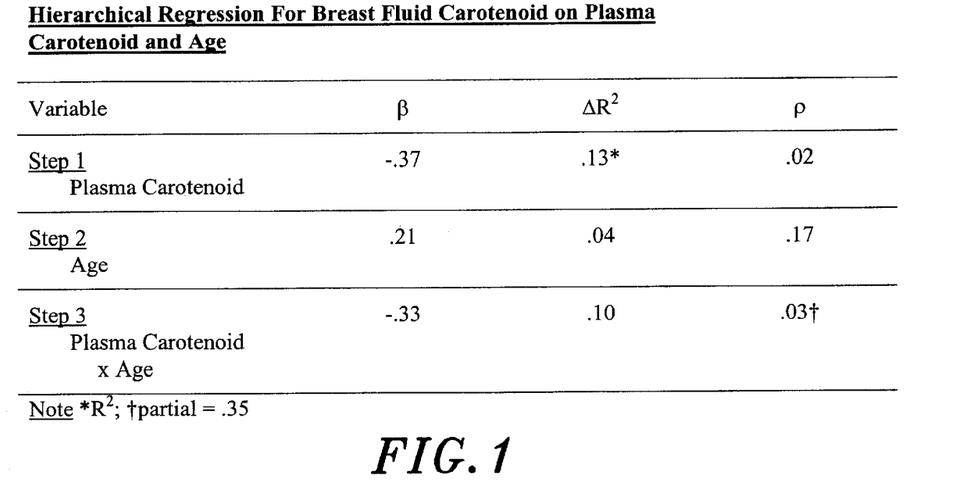
FIG. 1 shows the hierarchial regression for breast fluid carotenoid on plasma carotenoid and age.
Figure 2:
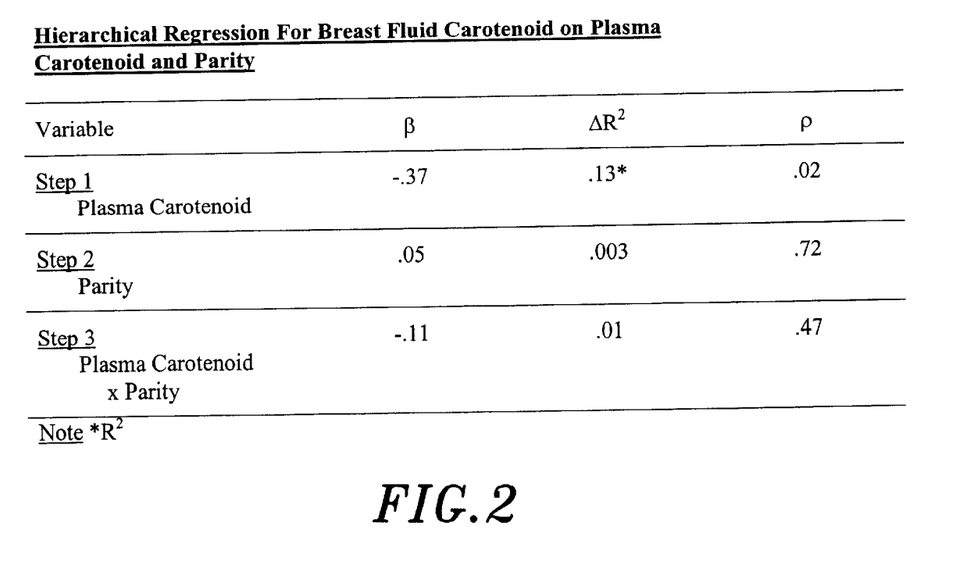
FIG. 2 shows the hierarchial regression for breast fluid carotenoid on plasma carotenoid and parity.
Figure 3:
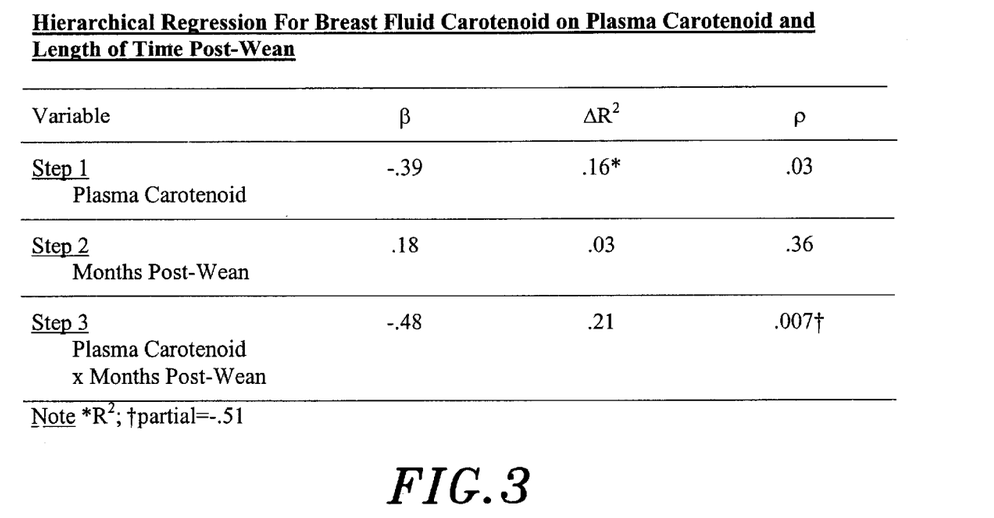
FIG. 3 shows the hierarchial regression for breast fluid carotenoid on plasma carotenoid and the length of time post wean.

Age significantly influenced the relation between plasma and breast fluid carotenoid levels, as illustrated in FIG. 1. A significant negative partial regression coefficient for plasma and age indicated a significant negative interaction. Thus, the relation between plasma and breast fluid carotenoid levels diminished with age. The results of the hierarchical regression did not support the influence of parity (See FIG. 2). The influence of length of time post-wean on the relation between plasma and breast fluid carotenoid levels was supported (see FIG. 3). Thus, the relation between plasma and breast fluid carotenoid levels diminished with the increasing duration of time since cessation of lactation.

Figure 4:
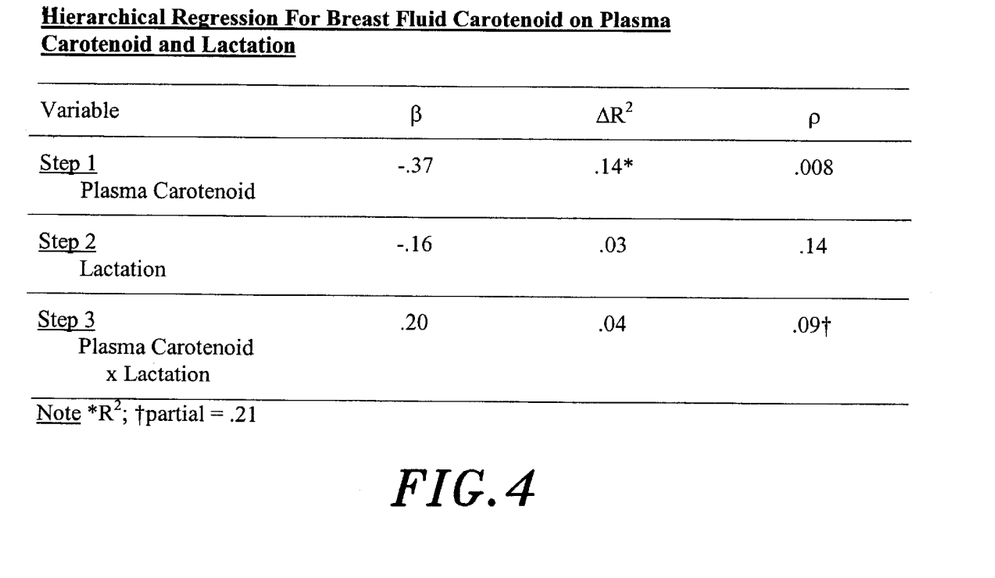
FIG. 4 shows the hierarchial regression for breast fluid carotenoid on plasma carotenoid and lactation.
Figure 5:
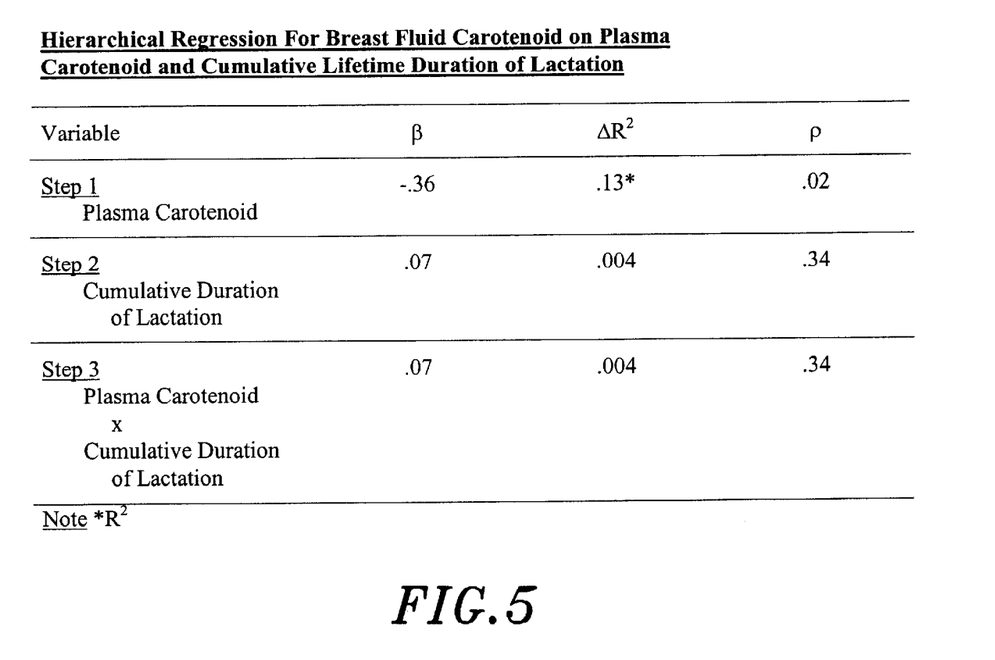
FIG. 5 shows the hierarchial regression for breast fluid carotenoid on plasma carotenoid and cumulative lifetime duration of lactation.
Figure 6:
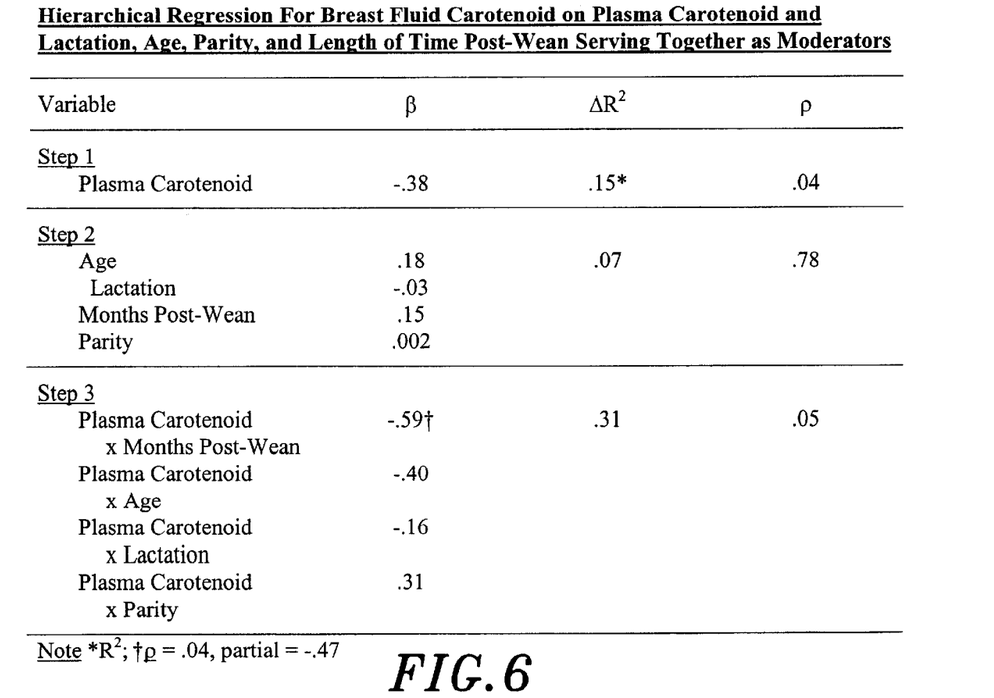
FIG. 6 shows the hierarchial regression for breast fluid carotenoid on plasma carotenoid and lactation, age, parity, and length of time post-wean serving together as moderators.

Hierarchical regression analysis with a one-tailed test of significance was used to examine the influence of lactation on the relation between plasma and breast fluid carotenoid levels. As illustrated in FIG. 4, the significant beta value in Step 3 of the hierarchical regression analysis, in addition to the significant change in the $R^2$ when the recent lactation entered the hierarchical regression equation with plasma carotenoid, signified the presence of an influence of recent lactation on the relation between plasma and breast fluid carotenoid levels. A significant positive partial regression coefficient for plasma carotenoid x lactation indicated a significant positive interaction. Thus, the hypothesized influence of lactation on the relation between plasma and breast fluid carotenoid levels was supported. Additionally, the longer a women breastfed her last child, the greater the positive relation between plasma and breast fluid carotenoid levels. However, results indicated that cumulative lifetime duration of lactation did not influence the relation between plasma and breast fluid carotenoid levels (see FIG. 5).

A significant negative partial regression coefficient for plasma carotenoid and length of time post-wean indicated a significant negative interaction. Thus, in the model, length of time post-wean diminished the relation between plasma and breast fluid carotenoid levels and altered the influence of recent lactation and age on the relation between plasma and breast fluid carotenoid levels.

Figure 7:
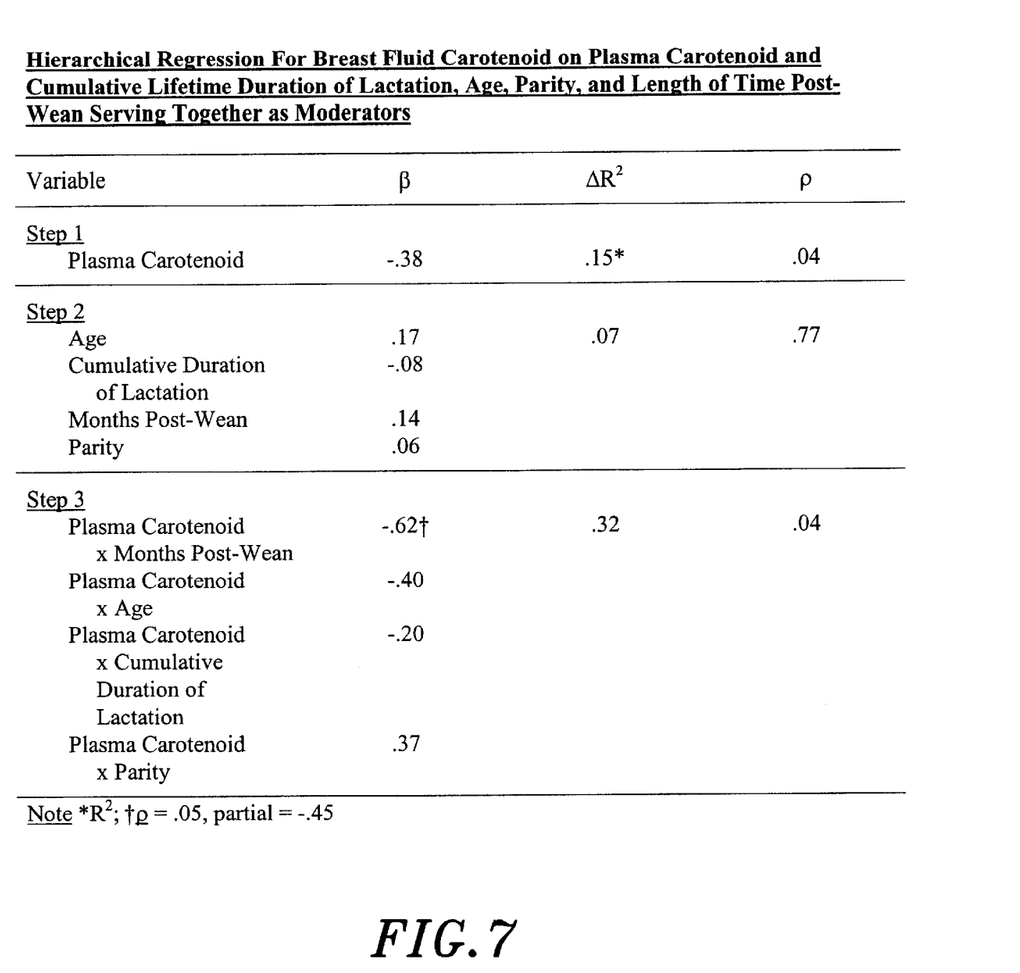
FIG. 7 shows the hierarchial regression for breast fluid carotenoid on plasma carotenoid and cumulative lifetime duration of lactation, age, parity, and length of time post-wean serving together as moderators.

A model derived from cumulative lifetime duration of lactation, age, parity, and length of time post-wean influenced the relation between plasma and breast fluid carotenoid levels (See FIG. 7). A negative partial regression coefficient for length of time post-wean indicated a significant negative influence. Thus, in the model, the influence of cumulative lifetime duration of lactation and parity was not altered, but age did not diminish the relation between plasma and breast fluid carotenoid levels as reported in separate analysis, while length of time post-wean did significantly diminish the relation between plasma and breast fluid carotenoid levels.

There were no significant differences between women on plasma or breast fluid carotenoid levels. The results also revealed that the longer a woman breasted her last child, the more likely she would obtain breast fluid. Additionally, the longer a woman breastfed her last child and the greater the reported total lifetime duration of lactation, the more likely the woman would secrete sufficient amounts of breast fluid for carotenoid analysis. This is not surprising if longer months of breastfeeding lead to greater adeptness at expressing milk, and therefore, aspirating breast fluid, even though the physiology of the two fluids differs. Aside from experiential considerations, there may be anatomical and physiologic changes that occur with lactation that increase the likelihood of aspirating breast fluid.

Age significantly influenced the relation between plasma and breast fluid carotenoid levels, with the relation between plasma and breast fluid carotenoid levels diminished as age increased, this was true for all women, regardless of lactation status. The American Cancer Society (1996b) reports that the incidence of breast cancer increases with age and breast cancer mortality rates increase for women 40–54 years of age. In epidemiological studies designed to investigate the protective effect of lactation and breast cancer risk, the independent protective effect of lactation was supported for premenopausal, but not postmenopausal, women (Byers et al., 1985), as also evident for carotenoids and risk (McTierman and Thomas, 1986; Yoo et al., 1992). Indeed, mammary involution at menopause represents a significant epithelial regression and loss followed by replacement of ductal and lobular structures by adipose tissue (Forbes, 1986). These anatomical changes result in a decreased blood flow and nutrient delivery. Thus, the changes which occur in the breast with the aging process may influence the delivery of micronutrients to the breast microenvironment.

Parity did not significantly influence the relation between plasma and breast fluid carotenoid levels, in past studies on risk of breast cancer, parity was often a confounding variable that when controlled revealed an independent protective effect of lactation. Parity did not moderate the relation between plasma and breast fluid carotenoid levels; however, parity may play its protective role as a mediating, or antecedent, factor, by offering further opportunity for lactation (Lindley & Walker, 1993).

A greater length of time post-wean significantly reduced the relation between plasma and breast fluid carotenoid levels. Results indicated that the relation between plasma and breast fluid carotenoid levels diminished the longer the time post-wean, which replicated Covington's data (Covington, et al., 1998). This is not surprising, since increasing number of months post-wean indicates a longer period of time away from the positive influence of lactation as a potentiating process. Additionally, post-lactation, the breast undergoes mammary involution over a three-month period of time, in which the number of mammary alveoli are reduced and blood flow and nutrient delivery is diminished (Lawrence, 1994; Neville & Niefert, 1983).

Lactation had a significant positive influence on the relation between plasma and breast fluid carotenoid levels. The results of previous epidemiological studies on lactation and breast cancer risk supports a protective effect, however the mechanism is unknown. Lactation, a physiologic process in which blood flow and nutrient transport to the breast increases, potentiates the delivery of available circulating plasma carotenoids into the microenvironment of the breast in women who breastfeed, especially at shorter periods post-wean. Lactation positively influenced the relation between plasma and breast fluid carotenoid levels. Additionally, the longer a woman breastfed her last child, the greater the relation between plasma and breast fluid carotenoid levels. This positive influence was detected at 15–35 months postpartum; the full duration of this potentiating action of lactation is yet to be demarcated.

The results of the analysis also indicated that cumulative lifetime duration of lactation did not influence the relation between plasma and breast fluid carotenoid levels. Indeed, this is a pertinent finding in that results of epidemiological studies supported the increasing cumulative lifetime duration of lactation and decreased risk of breast cancer (Ing, Ho, & Petrakis, 1977; Layde et al., 1988; Levin et al., 1964; Yuan et al., 1988). However, in these studies, cumulative lifetime duration of lactation was measured in number of years, often greater than five years. In this study, younger women who were 24 months postpartum were studied. Therefore, the mean cumulative duration of lactation in this study was short (20 months) in terms of lifetime influence. Additionally, the positive relation between cumulative lifetime duration of lactation and plasma carotenoid was an interesting finding. Perhaps women who have breastfed for longer periods of time over their lifespan have developed nutritionally-improved eating habits over time, or in general are indicative of a proxy group for healthy decisions and greater education.

A model derived from lactation, age, parity, and length of time post-wean on the relation between plasma and breast fluid carotenoid levels was supported. Furthermore, the influence of lactation on the relation was changed by the presence of age, parity, and length of time post-wean in the model. Whereas lactation does have a positive influence on the relation between plasma and breast fluid carotenoid levels, as indicated in separate analysis, the influence of length of time post-wean diminished the significance of the influence of recent lactation in this study. Thus, the duration of the potentiating influence of lactation appears strongest with increasing length of lactation to less than three months post-wean, before post-lactation mammary involution is completed. Furthermore, a model derived from cumulative lifetime duration of lactation, age, parity, and length of time post-wean significantly influenced the relation between plasma and breast fluid carotenoid levels was also supported. However, length of time post-wean accounted for the significant interaction effect. Additionally, the influence of age was not significant. Thus, length of time post-wean exerted a stronger diminishing influence on the relation between plasma and breast fluid carotenoid levels than did age. However, two facts are critical to the interpretation of these results. First, cumulative lifetime duration of lactation reported by the younger women in this study was considerably less than cumulative lifetime duration of lactation reported by older women in epidemiological studies supporting a protective effect of lifetime duration of lactation and breast cancer risk. In light of the mammary involution that occur with menopause (Forbes, 1986), the increased incidence of breast cancer may be related to the loss of chemopreventive substances available in the breast. The women in this study were not representative of a population of menopausal women.

The following considerations can be made within the limitations of the study. First, based on the moderator influence of lactation, choice of feeding an infant has dramatic health implications for women, in addition to the recognized health benefits of breastfeeding for the infant. Although these results are preliminary, the findings suggest a relation between lactation and the delivery of anticarcinogenic substances into the breast environment. Furthermore, the delivery of these carotenoids from the blood to the breast appears to be enhanced by increasing duration of lactation of the last child, but not by cumulative duration of lactation, at least early on when cumulative breastfeeding longevity has not yet been established. Additionally, other characteristics of individuals, such as older age and longer length of time post-wean, diminished the relation between plasma and breast fluid carotenoid levels. Still, lactation positively influenced the delivery of chemopreventive substances available in the blood to the breast ducts, where 90% of breast cancer is initiated.

In view of the foregoing, the present invention provides a method of systematically removing intraductal fluid from a non lactating breast. Preferably, this is accomplished by removing fluid on a sufficient number of occasions to maintain a reduced level of intraductal contaminants, but not with sufficient frequency to induce relactation. For many women, relactation will be induced by intraductal fluid aspiration for 15 minute sessions conducted once every four hours for from about 5 to about ten days. The frequency contemplated by the present inventors, on the other hand, is insufficient to induce relactation in the normal patient. Thus, maximum frequencies contemplated by the present inventors are on the order of no more than about 5 sessions per week, and generally no more than about one session per week. As a practical matter, patient motivation may not be high enough to sustain more than about 8 to 20 aspiration sessions per year for most patients.

Aspiration frequencies at a rate of at least about 6 sessions, preferably at least about 12 sessions, and more preferably at least about 18 sessions per year, but no more than the maximum discussed above are contemplated. In excess of about 24 sessions per year may further enhance the preventative properties of the present method. Even a single session per year, such as in conjunction with an annual exam, is believed to exhibit a risk reduction effect compared to no aspiration sessions. Thus, one or two or three or more sessions per year are also contemplated by the present inventors.

Prior to each aspiration session, keratin plug removal may be assisted by topical application of any of a variety of keratin softening agents such as $H_2O_2$, baking soda, or Debrox™, as is understood in the art. Ultrasonic vibration may also be used.

Figure 8:
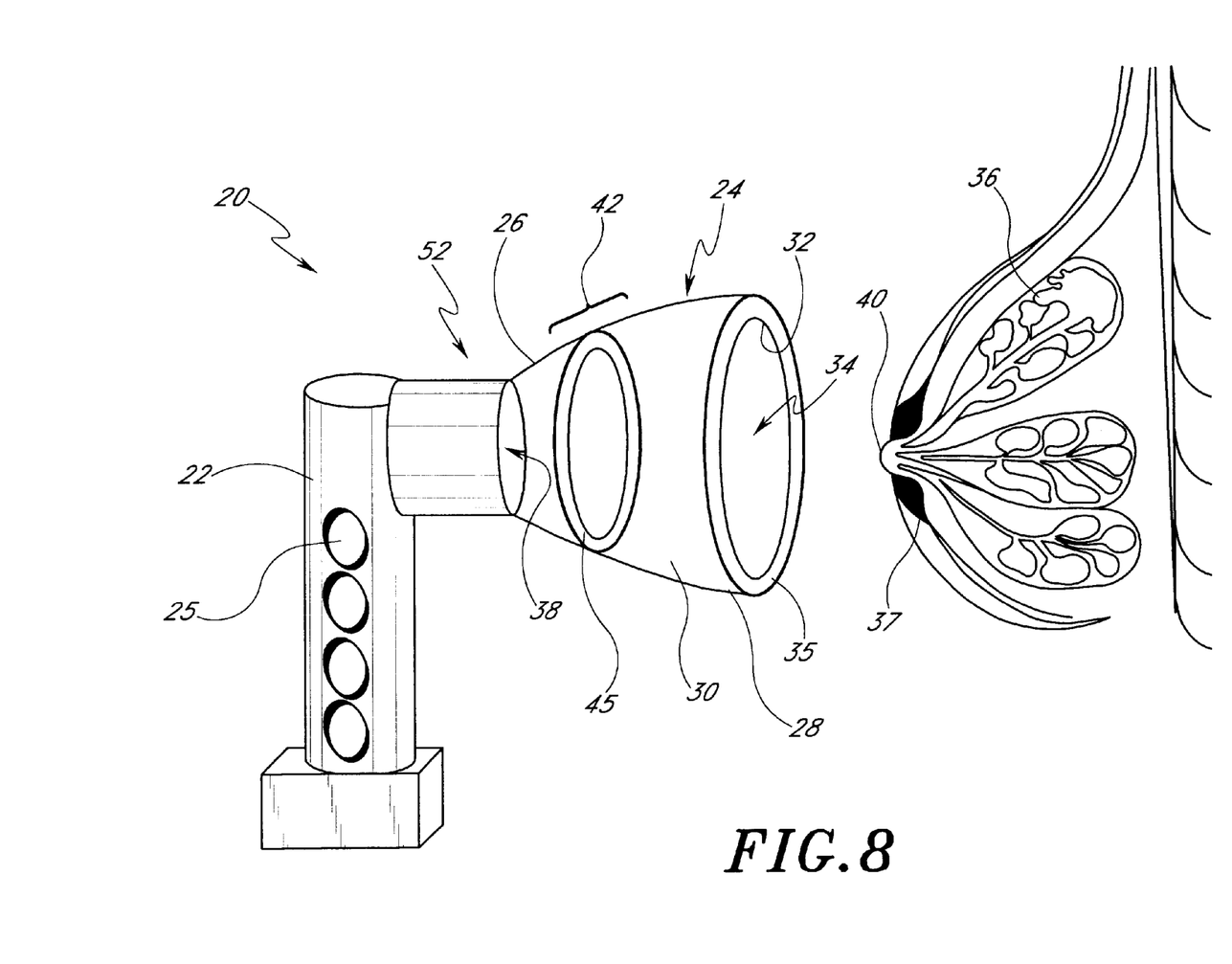
FIG. 8 is a schematic illustration of a portable, self-contained intraductal fluid aspiration device.

Referring to FIG. 8, there is illustrated a schematic representation of a portable, self-contained intraductal fluid aspiration device 20 in accordance with one aspect of the present invention. The aspiration device 20 includes a housing 22, for containing various controls and functional components of the device 20. One or more controls and/or indicators 25 may be provided on the housing, for controlling various aspects of the device such as suction, compression, and other features (e.g., heat, ultrasound) which may be included depending upon the intended functionality of the aspiration device 20. The housing 22 may be formed by extrusion, injection molding or other well known techniques from a suitable biocompatible material such as high density polyethylene, nylon, polyethylene terephthalate, or others well known in the art. The housing is preferably formed in an ergonomic configuration, to comfortably facilitate grasping in one hand during use.

The housing 22 is provided with a breast interface 24, which may either be permanently attached to the housing 22 or removably attached such as for cleaning or disposal. Breast interface 24 has a proximal end 26, a distal end 28, and a flexible body 30 extending therebetween. The interface 24 has a tissue contacting surface 32 defining a first concavity 34 for receiving a breast 36 and a second concavity 38 for receiving a nipple 40. The tissue contacting surface 32 may be an integral surface on the flexible body 30, or may comprise a separate interior liner which is adhered to or otherwise secured to the flexible body 30.

Flexible body 30 may be manufactured in any of a variety of ways, such as injection molding, blow molding tube stock within a tapered capture tube, or other known manners, using any of a variety of well known biocompatible polymeric materials. Preferably, the flexible body 30 is transparent, which may be achieved by forming from polycarbonate, or other relatively clear materials known in the art.

The dimensions of the interface 24 may be varied widely, as will be appreciated by those of skill in the art in view of the disclosure herein. In general, the distal end 28 of the flexible body 30 is provided with an elastic sealing ring 35 having an inside diameter within the range of from about 2"

to about 10". The distal limit of the second concavity 38 has an inside diameter within the range of from about 1" to about 4". The first concavity 34 has an axial length from proximal end 26 to distal end 28 within the range of from about 0" to about 12". The first concavity 34 has a generally conical or bell shaped interior configuration, as will be appreciated by those of skill in the art.

Preferably, the breast interface 24 is provided with a dynamic compression zone 42, having one or more compression elements 45 for compression in the mid breast region to facilitate intraductal fluid aspiration. Although the specific dimensions will vary from patient to patient, as well as with age and parity, the breast 36 includes a plurality of ducts 37 which are generally confluent in the direction of a plurality of external openings on the nipple 40. Most of the intraductal volume is contained in the distal one-half or one-third of the breast 36 (from the patient's perspective). Thus, the inventors presently believe that a compression zone 42 approximately centered around the midbreast region will optimize fluid transport in the duct.

Figure 9:
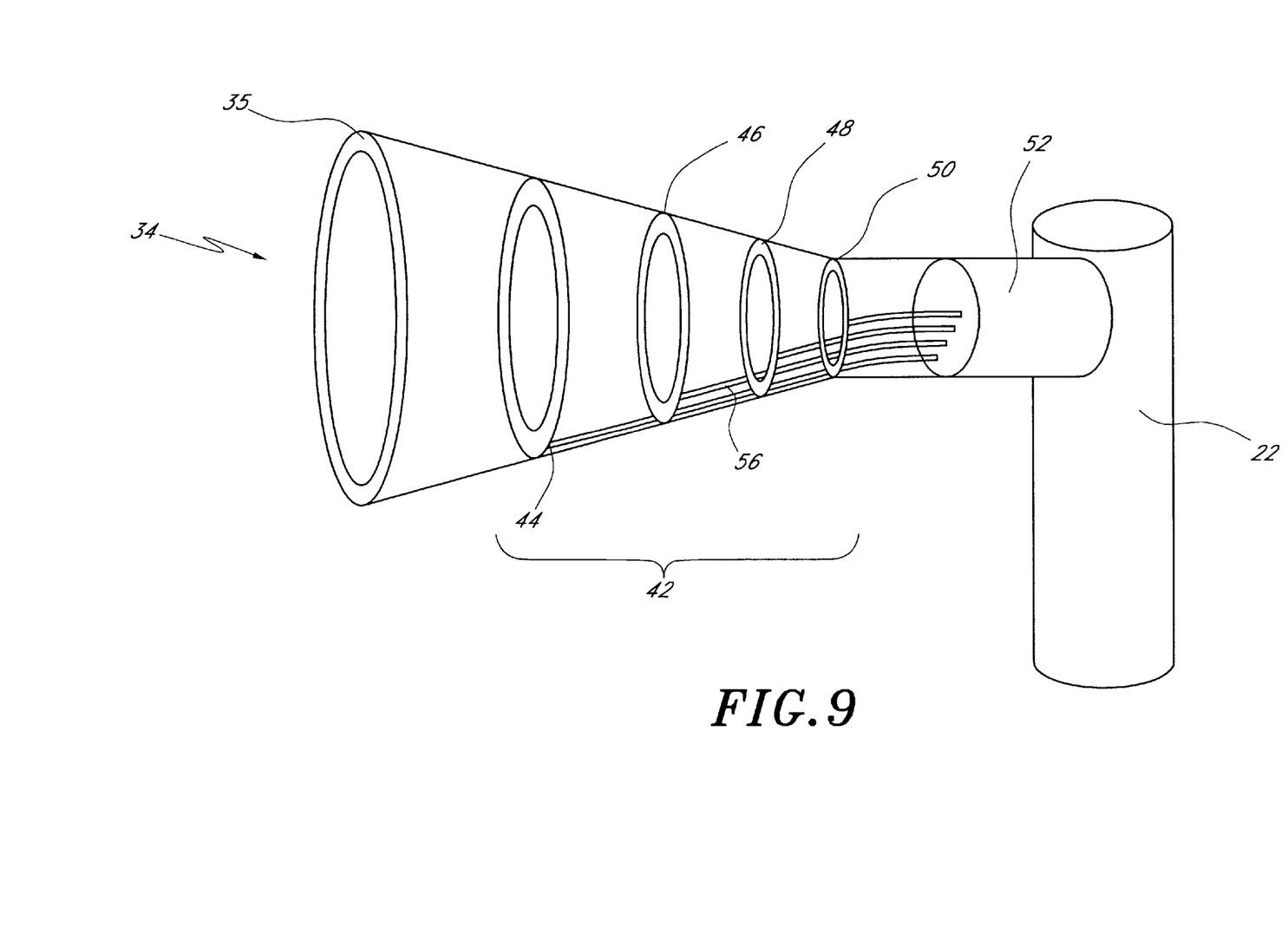
FIG. 9 is an illustration of a portable, self-contained intraductal fluid aspiration device as in FIG. 8, schematically illustrating a plurality of annular compression rings.

Referring to FIG. 9, the dynamic compression zone 42 is schematically illustrated (not to scale) as comprising a plurality of annular compression rings 44, 46, 48 and 50. Preferably, the annular compression rings are in operative communication with a driver 52 in the housing 22, to permit sequential operation. The preferred operation mode mimics a peristaltic motion such that tissue compression is accomplished sequentially starting with compression ring 44 followed by compression ring 46 followed by compression ring 48 followed by compression ring 50. As will be apparent to those of skill in the art in view of the disclosure herein, any of a wide variety of compression ring numbers and configurations may be utilized in accordance with the present invention. Thus, the illustration of four compression rings in FIG. 9 is not considered limiting on the scope of the invention. In general, anywhere from about one to about twenty compression elements 45 may be utilized, and, preferably, between about three and ten are contemplated in most embodiments.

The compression elements 45 may comprise any of a variety of structures, such as inflatable tubular elements or other inflatable structures, or mechanical compression elements such as rollers. In the illustrated embodiment, which is not drawn to scale in order to improve clarity, the dynamic compression zone 42 comprises a plurality of annular, inflatable, tubular compression rings each of which is connected to the driver 52 by a unique conduit 56. The driver 52 preferably includes a microprocessor or other central processing unit for sequentially driving the compression elements 45 as described previously. In one embodiment, the driver 52 includes a pump for controllably inflating and deflating each compression ring in response to the microprocessor and in accordance with the predetermined compression protocol. Inflation media such as air, water, or gel may be utilized, depending upon the desired performance characteristics. In one embodiment, a heat retaining gel such as morphing gel, available from Dow Coming, is utilized to enable the delivery of heat during the compression cycle.

The microprocessor may be programmed to a particular pumping and compression cycle characteristic, or may be adjustable by the user to optimize the aspiration function as desired. For example, compression cycles may be constant, with a sequential compression pattern from chest wall to the pump end. Alternatively, the compression cycle may be peristaltic or pulsitile. Vacuum may be applied constantly throughout the pumping cycle, or may be pulsitile either in phase or out of phase with the compression cycles.

The aspiration device 20 is further provided with a vacuum generator such as a pump in the housing 22, in communication with the second concavity 38 by way of a vacuum conduit (not shown). Associated electronics, such as a power source and driving circuitry are preferably connected to a control 25 to enable the user to selectively activate and deactivate the vacuum. Preferably, the pump is capable of generating a vacuum within an operating range of from 0 (pump off) to about 300 mm/Hg. Although vacuum in excess of 300 mm/Hg may also be utilized, vacuum in this area or higher may cause rupture of microvasculature and is unnecessary to accomplish the objectives of the present invention. For this reason, limit valves may be provided in communication with the vacuum conduit, as are known in the art, to limit the vacuum to no more than about 200 mm/Hg, or 250 mm/Hg, or 300 mm/Hg.

The foregoing embodiment is useful in a variety of settings, particularly for in home intraductal aspiration. In an alternative embodiment of the present invention, a desk top unit 60 is provided, such as for the physician's office or other more conventional clinical setting. See FIG. 10. The desk top intraductal fluid aspiration system 60 comprises a control unit 62, in communication with a power head 64 by way of an elongate flexible control line 66. The power head 64 is provided with a disposable user interface 68 which may be similar or identical to the interface 24 described previously. In this embodiment, the interface 68 is preferably removably connected to the power head 64, to facilitate one time use and subsequent disposal of the interface 68.

Figure 10:
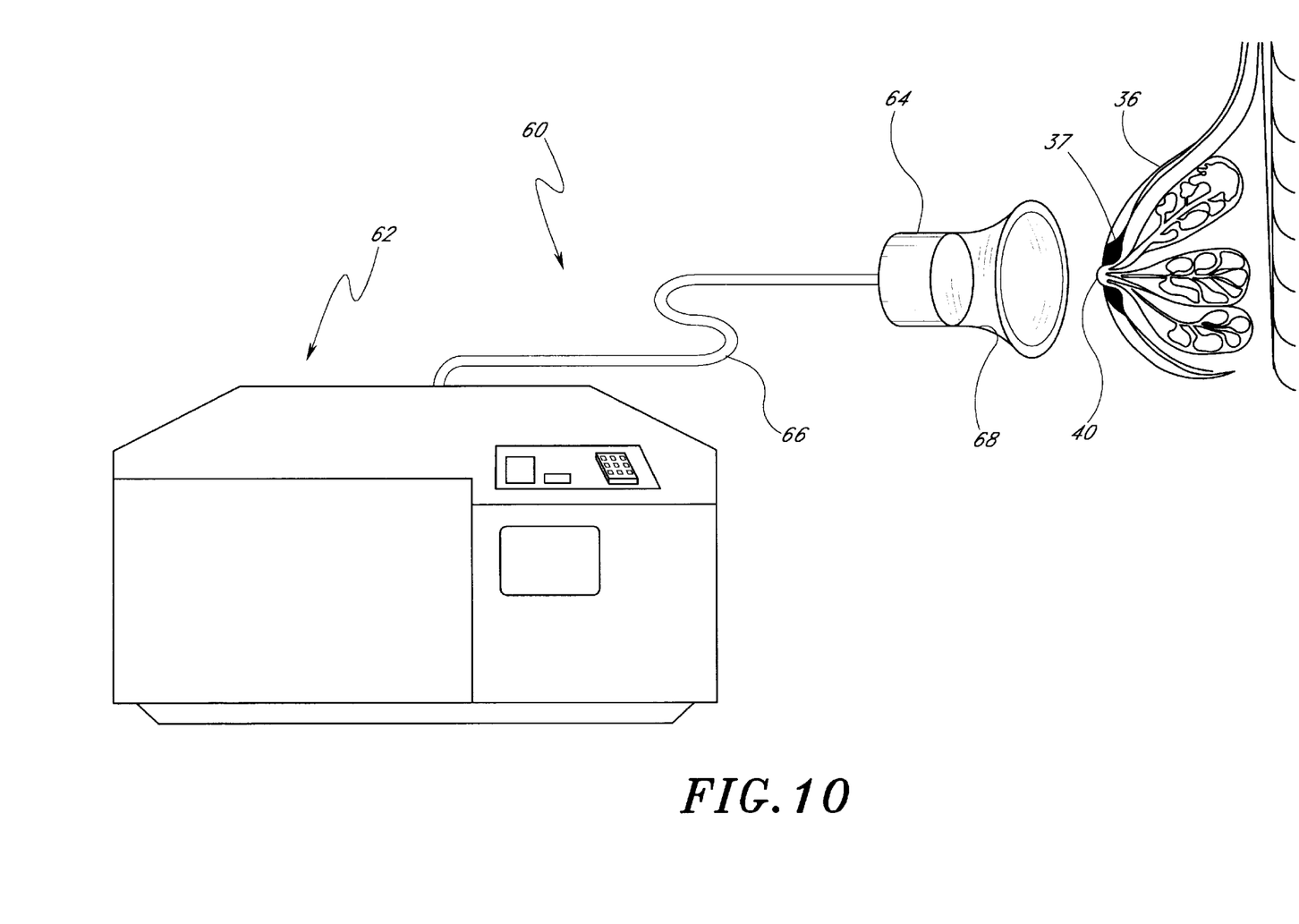
FIG. 10 is a schematic illustration of a desk top embodiment of an intraductal fluid aspiration device in accordance with the present invention.

The control 62 preferably includes the vacuum pump, and other driver circuitry and controls as may be needed depending upon the intended functionality of the desk top unit 60. For example, a vacuum pump (not illustrated) is in communication with the disposable user interface 68 by way of a vacuum lumen (not illustrated) extending throughout the length of the control line 66. Additional lumens or wiring extend through the control line 66 for accomplishing the peristaltic or other sequential compression motion of the dynamic compression zone 42 as has been discussed.

In a non-diagnostic embodiment, a reservoir is preferably positioned in fluid communication with the disposable user interface 68, to allow disposal of collected intraductal fluid. A removable sample collection container may alternatively be provided, such as to enable transport of collected intraductal fluid to a diagnostic laboratory or other facility for diagnostic analysis.

Preferably, the disposable user interface 68 is provided with a heat source, such as a heat retaining gel or other media for inflating the compression elements as has been previously discussed. Alternatively, resistance heating elements may be provided in the disposable user interface 68 or associated power head 64, powered by way of electrical conductors extending throughout the control line 66. In an embodiment where the dynamic compression zone 42 includes elements filled with a heat retaining gel or other media for retaining heat, the breast interface 24 may be removed and heated such as in a microwave oven or other heat source prior to use. An ultrasound source may also be provided in the control unit 62 or power head 64, for driving one or more ultrasound transducers in the power head 64 to assist in initial removal of keratin plugs that may occur at the opening of the ducts, and possibly also to serve as a heating source.

Although the present invention has been described in terms of certain preferred embodiments, it may be incorporated into or accomplished by other embodiments, by persons of ordinary skill in the art in view of the disclosure herein. The scope of the invention is therefore not intended to be limited by the specific embodiments disclosed herein, but is instead intended to be defined by the fall scope of the following claims.

What is claimed is:

1. An intraductal breast fluid aspiration device, comprising:
   a tissue contacting surface defining a first concavity for receiving a breast and a second concavity for receiving a nipple;
   a driver, for imparting compressive force on at least the portion of the tissue contacting surface defining the first concavity;
   a vacuum conduit in communication with the second concavity; and
   a binding system comprises a monoclonal antibody for binding at least one analyte of interest in the breast fluid in communication with the second concavity.

2. An intraductal breast fluid aspiration device as in claim 1, wherein the driver imparts peristaltic compressive force on the tissue contacting surface.

3. An intraductal breast fluid aspiration device as in claim 1, further comprising a heat source thermally coupled to the tissue contacting surface.

4. An intraductal breast fluid aspiration device as in claim 1, wherein the driver comprises a motor.

5. An intraductal breast fluid aspiration device as in claim 1, wherein the driver comprises at least one expandable chamber.

6. An intraductal breast fluid aspiration device as in claim 5, wherein the chamber is defined within a flexible tube.

7. An intraductal breast fluid aspiration device as in claim 1, further comprising a vacuum source in communication with the vacuum conduit.

8. An intraductal breast fluid aspiration device as in claim 1, wherein the sample collector comprises a hollow container.

9. An intraductal breast fluid aspiration device as in claim 8, wherein the container is removable from the aspiration device.

10. An intraductal breast fluid aspiration device as in claim 1, wherein the sample collector comprises an absorbent media.

11. An intraductal breast fluid aspiration device as in claim 1, further comprising a microprocessor for controlling the driver.

12. An intraductal breast fluid aspiration device as in claim 1, further comprising a housing, wherein the tissue contacting surface is removably carried by the housing.

13. A portable, self contained, intraductal fluid aspiration device, comprising:
    a housing;
    a breast interface on the housing;
    a heating element in thermal communication with the interface;
    a vacuum source in communication with the interface;
    a compression driver coupled to the interface; and
    at least one control on the housing for controlling operation of the aspiration device.

14. A portable, self contained, intraductal fluid aspiration device as in claim 13, wherein the interface is removably connected to the housing.

15. A portable, self contained, intraductal fluid aspiration device as in claim 13, further comprising a fluid reservoir in communication with the interface.

16. A portable, self contained, intraductal fluid aspiration device as in claim 13, wherein the fluid reservoir is removably attached to the housing.

17. A portable, self contained, intraductal fluid aspiration device as in claim 13, further comprising an ultrasonic transducer in communication with the interface.

18. An intraductal breast fluid aspiration device, comprising:
    a tissue contacting surface defining a first concavity for receiving a breast and a second concavity for receiving a nipple;
    a heat source thermally coupled to the tissue contacting surface;
    a driver, for imparting compressive force on at least the portion of the tissue contacting surface defining the first concavity;
    a vacuum conduit in communication with the second concavity; and
    a sample collector in communication with the second concavity.

19. An intraductal breast fluid aspiration device as in claim 18, wherein the driver imparts peristaltic compressive force on the tissue contacting surface.

20. An intraductal breast fluid aspiration device as in claim 18, further comprising a housing, wherein the tissue contacting surface is removably carried by the housing.

21. An intraductal breast fluid aspiration device as in claim 18, wherein the driver comprises a motor.

22. An intraductal breast fluid aspiration device as in claim 18, wherein the driver comprises at least one expandable chamber.

23. An intraductal breast fluid aspiration device as in claim 22, wherein the chamber is defined within a flexible tube.

24. An intraductal breast fluid aspiration device as in claim 18, further comprising a vacuum source in communication with the vacuum conduit.

25. An intraductal breast fluid aspiration device as in claim 18, wherein the sample collector comprises a hollow container.

26. An intraductal breast fluid aspiration device as in claim 25, wherein the container is removable from the aspiration device.

27. An intraductal breast fluid aspiration device as in claim 18, wherein the sample collector comprises an absorbent media.

28. An intraductal breast fluid aspiration device as in claim 18, wherein the sample collector comprises a binding system for binding at least one analyte of interest in the breast fluid.

29. An intraductal breast fluid aspiration device as in claim 28, wherein the binding system comprises a monoclonal antibody.

30. An intraductal breast fluid aspiration device as in claim 18, further comprising a microprocessor for controlling the driver.

31. An intraductal fluid aspiration device, comprising:
    a control unit;
    a power head;
    a flexible control line connecting the power head to the control unit;
    a disposable user interface removably attached to the power head;
    a vacuum source in the control unit, in communication with the user interface through the control line;

a compression cycle generator in force transmitting contact with the user interface; and a central processing unit in the control unit for controlling the delivery of heat, compression and suction through the user interface.

32. An intraductal fluid aspiration device as in claim 31, further comprising an ultrasound transducer in the power head.

33. An intraductal fluid aspiration device, comprising:

a control unit;

a power head;

an ultrasound transducer in the power head;

a flexible control line connecting the power head to the control unit;

a disposable user interface removably attached to the power head;

a vacuum source in the control unit, in communication with the user interface through the control line; and a compression cycle generator in force transmitting contact with the user interface.

34. An intraductal fluid aspiration device as in claim 33, further comprising a central processing unit in the control unit for controlling the delivery of heat, compression and suction through the user interface.

35. An intraductal breast fluid aspiration device, comprising:

a tissue contacting surface defining a concavity for receiving a breast;

at least one compression element, for imparting compressive force on at least a portion of the tissue contacting surface;

a vacuum conduit in communication with the concavity; and a heat source thermally coupled to the tissue contacting surface.

36. An intraductal breast fluid aspiration device as in claim 35, wherein the compression element imparts peristaltic compressive force on the tissue contacting surface.

37. An intraductal breast fluid aspiration device as in claim 35, wherein the compression element imparts pulsitile compressive force on the tissue contacting surface.

38. An intraductal breast fluid aspiration device as in claim 35, further comprising a motor for driving the compression element.

39. An intraductal breast fluid aspiration device as in claim 35, wherein the compression element comprises at least one expandable chamber.

40. An intraductal breast fluid aspiration device as in claim 36, further comprising a vacuum source in communication with the vacuum conduit.

41. An intraductal breast fluid aspiration device as in claim 35, further comprising a microprocessor.

42. An intraductal breast fluid aspiration device as in claim 35, further comprising a housing, wherein the tissue contacting surface is removably carried by the housing.

43. An intraductal breast fluid aspiration device as in claim 35, wherein the tissue contacting surface is on a one time use disposable membrane.

44. An intraductal breast fluid aspiration device as in claim 41, wherein the microprocessor is programmed to a predetermined compression protocol.

45. An intraductal breast fluid aspiration device as in claim 35, comprising a compression zone approximately centered around the midbreast region.

46. An intraductal breast fluid aspiration device as in claim 35, comprising from about one to about twenty compression elements.

47. An intraductal breast fluid aspiration device as in claim 35, comprising from about three to about ten compression elements.

48. An intraductal breast fluid aspiration device as in claim 41, comprising a pump for controllably inflating and deflating the compression element in response to the microprocessor and in accordance with a predetermined compression protocol.

49. An intraductal breast fluid aspiration device as in claim 35, further comprising a limit valve for limiting vacuum in the vacuum conduit to no more than about 300 mm/Hg.

50. An intraductal breast fluid aspiration device as in claim 35, further comprising a limit valve for limiting vacuum in the vacuum conduit to no more than about 250 mm/Hg.

51. An intraductal breast fluid aspiration device as in claim 35, further comprising a limit valve for limiting vacuum in the vacuum conduit to no more than about 200 mm/Hg.

52. An intraductal breast fluid aspiration device as in claim 35, further comprising a power head, wherein the compression element is carried by the power head.

53. An intraductal breast fluid aspiration device as in claim 52, further comprising an elongate flexible control line attached to the power head.

54. An intraductal breast fluid aspiration device as in claim 52, further comprising a disposable user interface, removably carried by the power head.

55. An intraductal breast fluid aspiration device as in claim 53, further comprising a control unit, wherein the power head is connected to the control unit by the elongate flexible control line.

56. An intraductal breast fluid aspiration device as in claim 55, wherein the heat source comprises a heat retaining media.

57. An intraductal breast fluid aspiration device as in claim 55, wherein the heat source comprises a resistive heating element.

58. An intraductal breast fluid aspiration device as in claim 55, comprising from about one to about twenty compression elements.

59. An intraductal breast fluid aspiration device as in claim 55, comprising from about three to about ten compression elements.

* * * * *